US012735666B2

(12) United States Patent
Parchment et al.

(10) Patent No.: US 12,735,666 B2
(45) Date of Patent: Sep. 15, 2026

(54) INSERT FOR PREPARING CELL CULTURE CHAMBERS

(71) Applicant: The United States of America,as represented by the Secretary,Department of Health and Human Services, Bethesda, MD (US)

(72) Inventors: Ralph E. Parchment, Frederick, MD (US); Thu A. Nguyen, Manhattan, KS (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 647 days.

(21) Appl. No.: 18/018,762

(22) PCT Filed: Jul. 30, 2021

(86) PCT No.: PCT/US2021/043930

§ 371 (c)(1),
(2) Date: Jan. 30, 2023

(87) PCT Pub. No.: WO2022/026846

PCT Pub. Date: Feb. 3, 2022

(65) Prior Publication Data

US 2023/0295550 A1 Sep. 21, 2023

Related U.S. Application Data

(60) Provisional application No. 63/058,794, filed on Jul. 30, 2020.

(51) Int. Cl.
*C12M 1/12* (2006.01)

(52) U.S. Cl.
CPC .................................. *C12M 25/14* (2013.01)

(58) Field of Classification Search
CPC ..................................................... C12M 25/14
See application file for complete search history.

(56) References Cited

U.S. PATENT DOCUMENTS 8,835,395 B2 9/2014 Sun et al.
2006/0166247 A1* 7/2006 Abbud-Antaki ....... C12M 25/14 435/6.16
2009/0136583 A1 5/2009 Park et al.
2016/0030629 A1 2/2016 Sun et al.
(Continued)

FOREIGN PATENT DOCUMENTS

FR 3 061 203 A1 6/2018
WO WO 2007/087402 A2 8/2007
(Continued)

OTHER PUBLICATIONS

Ali A et al. Protocol for in vitro establishment and long-term culture of mouse vaginal organoids. STAR Protocols 1: 100088. 10 pages. (Year: 2020).*

(Continued)

*Primary Examiner* — Lora E Barnhart Driscoll
(74) *Attorney, Agent, or Firm* — Leydig, Voit & Mayer, Ltd.

(57) ABSTRACT

Provided are inserts (100) for preparing a cell culture chamber(s), or array of chambers, inside of histology cassettes that are suitable for three-dimensional multicellular growth of a cell or cells into spheroids, organoids, or other 3D structures, such that the resulting 3D multi-cellular structures are ready and suitable for histology processing without transfer to a different receptacle or container. Further embodiments of the invention provide methods of preparing at least one cell culture chamber using the inserts, systems for growing three-dimensional multicellular spheroids comprising culturing cells within a cell culture chamber prepared using the inserts, and systems for analyzing at least (Continued)

one cultured cell in vitro comprising culturing cells within a cell culture chamber prepared using the inserts.

20 Claims, 4 Drawing Sheets

Specification includes a Sequence Listing.

(56) References Cited

U.S. PATENT DOCUMENTS

| | | | | |
|---|---|---|---|---|
| 2016/0175800 | A1* | 6/2016 | Murphy | G01N 33/5026 506/18 |
| 2017/0189334 | A1* | 7/2017 | Sun | A61K 9/06 |
| 2017/0261407 | A1 | 9/2017 | Kuh et al. | |
| 2018/0011408 | A1 | 1/2018 | Hribar et al. | |
| 2018/0071348 | A1* | 3/2018 | Conner | A61K 40/17 |
| 2019/0106667 | A1* | 4/2019 | Hribar | B01L 3/502 |
| 2021/0030811 | A1* | 2/2021 | Kim | A61K 9/0073 |
| 2021/0107961 | A1* | 4/2021 | Gellert | C07K 14/5443 |
| 2021/0277360 | A1* | 9/2021 | Nguyen | C12N 5/0697 |
| 2022/0249661 | A1* | 8/2022 | Hong | C07K 16/241 |

FOREIGN PATENT DOCUMENTS

| | | | |
|---|---|---|---|
| WO | WO 2009/042231 | A2 | 4/2009 |
| WO | WO 2014/089472 | A1 | 6/2014 |
| WO | WO 2019/213093 | A1 | 11/2019 |
| WO | WO 2020/018418 | A1 | 1/2020 |

OTHER PUBLICATIONS

Xu J et al. 3D h9e peptide hydrogel: An advanced three-dimensional cell culture system for anticancer prescreening of chemopreventive phenolic agents. Toxicol In Vitro 61: 104599. 8 pages. (Year: 2019).*

Huang H et al. Design of a shear-thinning recoverable peptide hydrogel from native sequences and application for influenza H1N1 vaccine adjuvant. Soft Matter 7:8905-8912. (Year: 2011).*

European Patent Office, International Search Report and Written Opinion issued in International Patent Application No. PCT/US2021/043930, mailed on Nov. 22, 2021.

Frith et al., "Tailored integrin-extracellular matrix interactions to direct human mesenchymal stem cell differentiation", *Stem Cells and Development*, 21(13): 2442-2456 (2012).

Huang et al., "Peptide Hydrogelation and Cell Encapsulation for 3D Culture of MCF-7 Breast Cancer Cells", *PLoS One*, 8(3): e59482 (pp. 1-15) (2013).

Ivanov et al., "Spheroid arrays for high-throughput single-cell analysis of spatial patterns and biomarker expression in 3D", *Scientific Reports*, 7: 41160 (pp. 1-12) (2017).

Ma et al., "Novel Linear Peptides with High Affinity to αvβ3 Integrin for Precise Tumor Identification", *Theranostics*, 7(6): 1511-1523 (2017).

Massia et al., "Covalently Immobilized Laminin Peptide Tyr-lle-Gly-Ser-Arg (YIGSR) Supports Cell Spreading and Co-localization of the 67-Kilodalton Laminin Receptor with α-Actinin and Vinculin", *Journal of Biological Chemistry*, 268(11): 8053-8059 (1993).

Säfholm et al., "A formylated hexapeptide ligand mimics the ability of Wnt-5a to impair migration of human breast epithelial cells", *Journal of Biological Chemistry*, 281(5): 2740-2749 (2006).

Sato et al., "Single Lgr5 stem cells build crypt-villus structures in vitro without a mesenchymal niche", *Nature*, 459(7244): 262-265 (2009).

Wayner et al., "Activation-dependent recognition by hematopoietic cells of the LDV sequence in the V region of fibronectin", *Journal of Cellular Biology*, 116(2): 489-497 (1992).

* cited by examiner

SEQUENCE LISTING

<160> NUMBER OF SEQ ID NOS: 54

<210> SEQ ID NO 1
<211> LENGTH: 19
<212> TYPE: PRT
<213> ORGANISM: Artificial Sequence
<220> FEATURE:
<223> OTHER INFORMATION: synthetic

<400> SEQUENCE: 1

Phe Leu Ile Val Ile Gly Ser Ile Ile Gly Pro Gly Gly Asp Gly Pro
1 5 10 15

Gly Gly Asp

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Phe Leu Ile Val Ile
1 5

```
<210> SEQ ID NO 3
<211> LENGTH: 4
<212> TYPE: PRT
<213> ORGANISM: Artificial Sequence
<220> FEATURE:
<223> OTHER INFORMATION: synthetic

<400> SEQUENCE: 3

Gly Ser Ile Ile
1


<210> SEQ ID NO 4
<211> LENGTH: 10
<212> TYPE: PRT
<213> ORGANISM: Artificial Sequence
<220> FEATURE:
<223> OTHER INFORMATION: synthetic

<400> SEQUENCE: 4

Gly Pro Gly Gly Asp Gly Pro Gly Gly Asp
1               5                   10


<210> SEQ ID NO 5
<211> LENGTH: 5
<212> TYPE: PRT
<213> ORGANISM: Artificial Sequence
<220> FEATURE:
<223> OTHER INFORMATION: synthetic

<400> SEQUENCE: 5

Gly Leu Ile Val Ile
1               5


<210> SEQ ID NO 6
<211> LENGTH: 5
<212> TYPE: PRT
<213> ORGANISM: Artificial Sequence
<220> FEATURE:
<223> OTHER INFORMATION: synthetic

<400> SEQUENCE: 6

Pro Leu Ile Val Ile
1               5


<210> SEQ ID NO 7
<211> LENGTH: 5
<212> TYPE: PRT
<213> ORGANISM: Artificial Sequence
<220> FEATURE:
<223> OTHER INFORMATION: synthetic

<400> SEQUENCE: 7

Asp Leu Ile Val Ile
1               5


<210> SEQ ID NO 8
<211> LENGTH: 5
<212> TYPE: PRT
<213> ORGANISM: Artificial Sequence
<220> FEATURE:
<223> OTHER INFORMATION: synthetic

<400> SEQUENCE: 8

Val Leu Ile Val Ile
1               5


<210> SEQ ID NO 9
```

<211> LENGTH: 5
<212> TYPE: PRT
<213> ORGANISM: Artificial Sequence
<220> FEATURE:
<223> OTHER INFORMATION: synthetic

<400> SEQUENCE: 9

Ile Leu Ile Val Ile
1 5

<210> SEQ ID NO 10
<211> LENGTH: 5
<212> TYPE: PRT
<213> ORGANISM: Artificial Sequence
<220> FEATURE:
<223> OTHER INFORMATION: synthetic

<400> SEQUENCE: 10

Leu Leu Ile Val Ile
1 5

<210> SEQ ID NO 11
<211> LENGTH: 5
<212> TYPE: PRT
<213> ORGANISM: Artificial Sequence
<220> FEATURE:
<223> OTHER INFORMATION: synthetic

<400> SEQUENCE: 11

Ala Leu Ile Val Ile
1 5

<210> SEQ ID NO 12
<211> LENGTH: 5
<212> TYPE: PRT
<213> ORGANISM: Artificial Sequence
<220> FEATURE:
<223> OTHER INFORMATION: synthetic

<400> SEQUENCE: 12

Phe Gly Ile Val Ile
1 5

<210> SEQ ID NO 13
<211> LENGTH: 5
<212> TYPE: PRT
<213> ORGANISM: Artificial Sequence
<220> FEATURE:
<223> OTHER INFORMATION: synthetic

<400> SEQUENCE: 13

Phe Pro Ile Val Ile
1 5

<210> SEQ ID NO 14
<211> LENGTH: 5
<212> TYPE: PRT
<213> ORGANISM: Artificial Sequence
<220> FEATURE:
<223> OTHER INFORMATION: synthetic

<400> SEQUENCE: 14

Phe Asp Ile Val Ile
1 5

<210> SEQ ID NO 15
<211> LENGTH: 5

<212> TYPE: PRT
<213> ORGANISM: Artificial Sequence
<220> FEATURE:
<223> OTHER INFORMATION: synthetic

<400> SEQUENCE: 15

Phe Val Ile Val Ile
1 5

<210> SEQ ID NO 16
<211> LENGTH: 5
<212> TYPE: PRT
<213> ORGANISM: Artificial Sequence
<220> FEATURE:
<223> OTHER INFORMATION: synthetic

<400> SEQUENCE: 16

Phe Ile Ile Val Ile
1 5

<210> SEQ ID NO 17
<211> LENGTH: 5
<212> TYPE: PRT
<213> ORGANISM: Artificial Sequence
<220> FEATURE:
<223> OTHER INFORMATION: synthetic

<400> SEQUENCE: 17

Phe Ala Ile Val Ile
1 5

<210> SEQ ID NO 18
<211> LENGTH: 5
<212> TYPE: PRT
<213> ORGANISM: Artificial Sequence
<220> FEATURE:
<223> OTHER INFORMATION: synthetic

<400> SEQUENCE: 18

Phe Leu Gly Val Ile
1 5

<210> SEQ ID NO 19
<211> LENGTH: 5
<212> TYPE: PRT
<213> ORGANISM: Artificial Sequence
<220> FEATURE:
<223> OTHER INFORMATION: synthetic

<400> SEQUENCE: 19

Phe Leu Pro Val Ile
1 5

<210> SEQ ID NO 20
<211> LENGTH: 5
<212> TYPE: PRT
<213> ORGANISM: Artificial Sequence
<220> FEATURE:
<223> OTHER INFORMATION: synthetic

<400> SEQUENCE: 20

Phe Leu Asp Val Ile
1 5

<210> SEQ ID NO 21
<211> LENGTH: 5
<212> TYPE: PRT

<213> ORGANISM: Artificial Sequence
<220> FEATURE:
<223> OTHER INFORMATION: synthetic

<400> SEQUENCE: 21

Phe Leu Val Ile Val
1 5

<210> SEQ ID NO 22
<211> LENGTH: 5
<212> TYPE: PRT
<213> ORGANISM: Artificial Sequence
<220> FEATURE:
<223> OTHER INFORMATION: synthetic

<400> SEQUENCE: 22

Phe Leu Ala Val Ile
1 5

<210> SEQ ID NO 23
<211> LENGTH: 5
<212> TYPE: PRT
<213> ORGANISM: Artificial Sequence
<220> FEATURE:
<223> OTHER INFORMATION: synthetic

<400> SEQUENCE: 23

Phe Leu Ile Gly Ile
1 5

<210> SEQ ID NO 24
<211> LENGTH: 5
<212> TYPE: PRT
<213> ORGANISM: Artificial Sequence
<220> FEATURE:
<223> OTHER INFORMATION: synthetic

<400> SEQUENCE: 24

Phe Leu Ile Pro Ile
1 5

<210> SEQ ID NO 25
<211> LENGTH: 5
<212> TYPE: PRT
<213> ORGANISM: Artificial Sequence
<220> FEATURE:
<223> OTHER INFORMATION: synthetic

<400> SEQUENCE: 25

Phe Leu Ile Asp Ile
1 5

<210> SEQ ID NO 26
<211> LENGTH: 5
<212> TYPE: PRT
<213> ORGANISM: Artificial Sequence
<220> FEATURE:
<223> OTHER INFORMATION: synthetic

<400> SEQUENCE: 26

Phe Leu Ile Ile Ile
1 5

<210> SEQ ID NO 27
<211> LENGTH: 5
<212> TYPE: PRT
<213> ORGANISM: Artificial Sequence
<220> FEATURE:
<223> OTHER INFORMATION: synthetic

<400> SEQUENCE: 27

Phe Leu Ile Leu Ile
1 5

<210> SEQ ID NO 28
<211> LENGTH: 5
<212> TYPE: PRT
<213> ORGANISM: Artificial Sequence
<220> FEATURE:
<223> OTHER INFORMATION: synthetic

<400> SEQUENCE: 28

Phe Leu Ile Ala Ile
1 5

<210> SEQ ID NO 29
<211> LENGTH: 5
<212> TYPE: PRT
<213> ORGANISM: Artificial Sequence
<220> FEATURE:
<223> OTHER INFORMATION: synthetic

<400> SEQUENCE: 29

Phe Leu Ile Val Gly
1 5

<210> SEQ ID NO 30
<211> LENGTH: 5
<212> TYPE: PRT
<213> ORGANISM: Artificial Sequence
<220> FEATURE:
<223> OTHER INFORMATION: synthetic

<400> SEQUENCE: 30

Phe Leu Ile Val Pro
1 5

<210> SEQ ID NO 31
<211> LENGTH: 5
<212> TYPE: PRT
<213> ORGANISM: Artificial Sequence
<220> FEATURE:
<223> OTHER INFORMATION: synthetic

<400> SEQUENCE: 31

Phe Leu Ile Val Asp
1 5

<210> SEQ ID NO 32
<211> LENGTH: 5
<212> TYPE: PRT
<213> ORGANISM: Artificial Sequence
<220> FEATURE:
<223> OTHER INFORMATION: synthetic

<400> SEQUENCE: 32

Phe Leu Ile Val Val
1 5

<210> SEQ ID NO 33
<211> LENGTH: 5
<212> TYPE: PRT
<213> ORGANISM: Artificial Sequence
<220> FEATURE:

<223> OTHER INFORMATION: synthetic

<400> SEQUENCE: 33

Phe Leu Ile Val Leu
1 5

<210> SEQ ID NO 34
<211> LENGTH: 5
<212> TYPE: PRT
<213> ORGANISM: Artificial Sequence
<220> FEATURE:
<223> OTHER INFORMATION: synthetic

<400> SEQUENCE: 34

Phe Leu Ile Val Ala
1 5

<210> SEQ ID NO 35
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: wherein Xaa can be G, A, D, R, Q, E, S, T, K or P
<220> FEATURE:
<221> NAME/KEY: MISC_FEATURE
<222> LOCATION: (4)..(4)
<223> OTHER INFORMATION: wherein Xaa can be G, A, D, R, Q, E, S, T, K or P

<400> SEQUENCE: 35

Gly Pro Xaa Xaa Asp
1 5

<210> SEQ ID NO 36
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: wherein Xaa can be G, A, D, R, Q, E, S, T, K or P
<220> FEATURE:
<221> NAME/KEY: MISC_FEATURE
<222> LOCATION: (3)..(3)
<223> OTHER INFORMATION: wherein Xaa can be G, A, D, R, Q, E, S, T, K or P

<400> SEQUENCE: 36

Gly Xaa Xaa Pro Asp
1 5

<210> SEQ ID NO 37
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: wherein Xaa can be G, A, D, R, Q, E, S, T, K or P
<220> FEATURE:

<221> NAME/KEY: MISC_FEATURE
<222> LOCATION: (4)..(4)
<223> OTHER INFORMATION: wherein Xaa can be G, A, D, R, Q, E, S, T, K or P

<400> SEQUENCE: 37

Gly Xaa Pro Xaa Ile Asp
1 5

<210> SEQ ID NO 38
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: wherein Xaa can be G or A
<220> FEATURE:
<221> NAME/KEY: MISC_FEATURE
<222> LOCATION: (9)..(9)
<223> OTHER INFORMATION: wherein Xaa can be G or A

<400> SEQUENCE: 38

Gly Pro Gly Xaa Asp Gly Pro Gly Xaa Asp
1 5 10

<210> SEQ ID NO 39
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: wherein Xaa can be A, G, V, I, or L
<220> FEATURE:
<221> NAME/KEY: MISC_FEATURE
<222> LOCATION: (7)..(7)
<223> OTHER INFORMATION: wherein Xaa can be P, A, G, V, I, or L
<220> FEATURE:
<221> NAME/KEY: MISC_FEATURE
<222> LOCATION: (8)..(8)
<223> OTHER INFORMATION: wherein Xaa can be A, G, V, I, or L
<220> FEATURE:
<221> NAME/KEY: MISC_FEATURE
<222> LOCATION: (9)..(9)
<223> OTHER INFORMATION: wherein Xaa can be A, G, V, I, or L

<400> SEQUENCE: 39

Gly Pro Gly Xaa Asp Gly Xaa Xaa Xaa Asp
1 5 10

<210> SEQ ID NO 40
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: wherein Xaa can be of A, G, V, I, or L

<400> SEQUENCE: 40

Gly Pro Gly Xaa Asp
1 5

<210> SEQ ID NO 41

<211> LENGTH: 4
<212> TYPE: PRT
<213> ORGANISM: Artificial Sequence
<220> FEATURE:
<223> OTHER INFORMATION: synthetic

<400> SEQUENCE: 41

Gly Gly Gly Gly
1

<210> SEQ ID NO 42
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: wherein Xaa can be G, I, V, A, L, or S
<220> FEATURE:
<221> NAME/KEY: MISC_FEATURE
<222> LOCATION: (4)..(4)
<223> OTHER INFORMATION: wherein Xaa can be G, I, V, A, L, or S

<400> SEQUENCE: 42

Gly Ser Xaa Xaa
1

<210> SEQ ID NO 43
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa can be G, I, V, A, L, or S
<220> FEATURE:
<221> NAME/KEY: MISC_FEATURE
<222> LOCATION: (4)..(4)
<223> OTHER INFORMATION: wherein Xaa can be G, I, V, A, L, or S

<400> SEQUENCE: 43

Xaa Gly Ser Xaa
1

<210> SEQ ID NO 44
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa can be G, I, V, A, L, or S
<220> FEATURE:
<221> NAME/KEY: MISC_FEATURE
<222> LOCATION: (2)..(2)
<223> OTHER INFORMATION: wherein Xaa can be G, I, V, A, L, or S

<400> SEQUENCE: 44

Xaa Xaa Gly Ser
1

<210> SEQ ID NO 45
<211> LENGTH: 4
<212> TYPE: PRT
<213> ORGANISM: Artificial Sequence

```
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa can be G, I, V, A, L, or S
<220> FEATURE:
<221> NAME/KEY: MISC_FEATURE
<222> LOCATION: (4)..(4)
<223> OTHER INFORMATION: Xaa can be G, I, V, A, L, or S

<400> SEQUENCE: 45

Ser Gly Xaa Xaa
1


<210> SEQ ID NO 46
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa can be G, I, V, A, L, or S
<220> FEATURE:
<221> NAME/KEY: MISC_FEATURE
<222> LOCATION: (4)..(4)
<223> OTHER INFORMATION: wherein Xaa can be G, I, V, A, L, or S

<400> SEQUENCE: 46

Xaa Ser Gly Xaa
1


<210> SEQ ID NO 47
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa can be G, I, V, A, L, or S
<220> FEATURE:
<221> NAME/KEY: MISC_FEATURE
<222> LOCATION: (2)..(2)
<223> OTHER INFORMATION: wherein Xaa can be G, I, V, A, L, or S

<400> SEQUENCE: 47

Xaa Xaa Ser Gly
1


<210> SEQ ID NO 48
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: wherein Xaa can be G, I, V, A, L, or S
<220> FEATURE:
<221> NAME/KEY: MISC_FEATURE
<222> LOCATION: (4)..(4)
<223> OTHER INFORMATION: wherein Xaa can be G, I, V, A, L, or S

<400> SEQUENCE: 48

Gly Xaa Ser Xaa
1
```

<210> SEQ ID NO 49
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa can be G, I, V, A, L, or S
<220> FEATURE:
<221> NAME/KEY: MISC_FEATURE
<222> LOCATION: (3)..(3)
<223> OTHER INFORMATION: wherein Xaa can be G, I, V, A, L, or S

<400> SEQUENCE: 49

Xaa Gly Xaa Ser
1

<210> SEQ ID NO 50
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: wherein Xaa can be G, I, V, A, L, or S
<220> FEATURE:
<221> NAME/KEY: MISC_FEATURE
<222> LOCATION: (4)..(4)
<223> OTHER INFORMATION: wherein Xaa can be G, I, V, A, L, or S

<400> SEQUENCE: 50

Ser Xaa Gly Xaa
1

<210> SEQ ID NO 51
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa can be G, I, V, A, L, or S
<220> FEATURE:
<221> NAME/KEY: MISC_FEATURE
<222> LOCATION: (3)..(3)
<223> OTHER INFORMATION: wherein Xaa can be G, I, V, A, L, or S

<400> SEQUENCE: 51

Xaa Ser Xaa Gly
1

<210> SEQ ID NO 52
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: wherein Xaa can be G, I, V, A, L, or S
<220> FEATURE:
<221> NAME/KEY: MISC_FEATURE
<222> LOCATION: (3)..(3)
<223> OTHER INFORMATION: wherein Xaa can be G, I, V, A, L, or S

```
<400> SEQUENCE: 52

Gly Xaa Xaa Ser
1


<210> SEQ ID NO 53
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: wherein Xaa can be G, I, V, A, L, or S
<220> FEATURE:
<221> NAME/KEY: MISC_FEATURE
<222> LOCATION: (3)..(3)
<223> OTHER INFORMATION: wherein Xaa can be G, I, V, A, L, or S

<400> SEQUENCE: 53

Ser Xaa Xaa Gly
1


<210> SEQ ID NO 54
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa can be G, I, or V
<220> FEATURE:
<221> NAME/KEY: MISC_FEATURE
<222> LOCATION: (3)..(3)
<223> OTHER INFORMATION: wherein Xaa can be G, I, V, A, or L
<220> FEATURE:
<221> NAME/KEY: MISC_FEATURE
<222> LOCATION: (4)..(4)
<223> OTHER INFORMATION: wherein Xaa can be G, I, V, A, or L

<400> SEQUENCE: 54

Xaa Ser Xaa Xaa
1
```

INSERT FOR PREPARING CELL CULTURE CHAMBERS

CROSS-REFERENCE TO RELATED APPLICATIONS

This patent application is the U.S. national stage of International Patent Application No. PCT/US2021/043930, filed Jul. 30, 2021, which claims priority to and the benefit of U.S. Provisional Patent Application No. 63/058,794 filed Jul. 30, 2020, each of which is incorporated by reference in its entirety herein.

STATEMENT REGARDING FEDERALLY SPONSORED RESEARCH OR DEVELOPMENT

This invention was made with Government support under project number Z01N261200800001E by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 12.441 Byte ASCII (Text) file named "766666_ST25.txt," dated Jan. 20, 2023.

BACKGROUND OF THE INVENTION

Cell culture provides an important in vitro tool to understand in vivo systems. It is desirable to be able to easily and efficiently analyze cells that are cultured in three dimensions (3D). Currently, for analysis using microscopy, the cells must be cultured in culture vessels to form spheroids (single cell type), organoids (>1 cell type), or other multi-cellular population, and then the multicellular structures must be transferred to histology cassettes or containers for further processing (e.g., fixing, embedding, and sectioning). The cell transfer process is tedious, slow, increases the risk of errors, and requires additional materials (e.g., pipettes). Further, it is difficult to manually place and maintain more than one specimen of 3D multicellular structures in histology cassettes at the same axial registration (i.e., same vertical plane) such that following embedding, the more than one specimen are present and evaluable by microscopy within a single cut section from the paraffin block. Accordingly, there is a need for improved cell culture vessels, and methods of making such vessels, to improve analysis of 3D cultured cells.

BRIEF SUMMARY OF THE INVENTION

An embodiment of the invention provides an insert (100) for preparing a cell culture chamber, or an array of such chambers, comprising (a) a base (110) having a base top surface (114), a base bottom surface (115), and at least three base sides (111), and (b) at least one pillar (120) having a pillar top (124), a pillar bottom (125), a pillar first outer diameter (122*a*), a pillar second outer diameter (123*a*), and a pillar outside wall (127), wherein the at least one pillar bottom (125) is contiguous with the base top surface (114), the dimensions of the insert allow for (a) insertion of the at least one pillar (120) of the insert into a hydrogel that is within a histology cassette or (b) placing of a hydrogel around the at least one pillar (120) of the insert when it is in the histology cassette, the pillar second outer diameter (123*a*) creates a cell culture chamber within the hydrogel after the insert is removed from the hydrogel, and the cell culture chamber is suitable for three-dimensional multicellular spheroid growth within the cell culture chamber.

Another embodiment of the invention provides a method of preparing at least one cell culture chamber comprising (a) placing the at least one pillar of the insert of an embodiment of the invention into a hydrogel that is within a histology cassette, and (b) removing the insert from the hydrogel and the histology cassette to create the at least one cell culture chamber within the histology cassette.

A further embodiment of the invention provides a method of preparing at least one cell culture chamber comprising (a) placing the at least one pillar of the insert of an embodiment of the present invention within a histology cassette, (b) placing a hydrogel into the histology cassette, and (c) removing the insert from the hydrogel and the histology cassette to create the at least one cell culture chamber within the histology cassette.

Yet another embodiment of the invention provides a system for growing three-dimensional multicellular spheroids, organoids, or other multi-cellular structures comprising culturing cells within the at least one cell culture chamber prepared using the insert of an embodiment of the present invention to produce three-dimensional multicellular spheroids.

An additional embodiment of the invention provides a system for analyzing at least one cultured cell in vitro comprising (a) culturing a cell within the at least one cell culture chamber prepared using the insert of an embodiment of the present invention to produce three-dimensional multicellular spheroids, (b) fixing the three-dimensional multicellular spheroids within the at least one cell culture chamber, (c) embedding the three-dimensional multicellular spheroids within the at least one cell culture chamber, (d) sectioning the three-dimensional multicellular spheroids, (e) staining the three-dimensional multicellular spheroids, and (f) assessing the properties of the three-dimensional multicellular spheroids based on the level of staining, wherein the three-dimensional multicellular spheroids are cultured, fixed, and embedded while remaining within a single histology cassette.

BRIEF DESCRIPTION OF THE SEVERAL VIEWS OF THE DRAWING(S)

FIG. 1 shows an arrangement of 8 rows of 10 pillars.

FIG. 2 shows an arrangement of 2 rows of 4 pillars.

FIG. 4 shows an arrangement of 8 rows of 10 solid pillars.

DETAILED DESCRIPTION OF THE INVENTION

Figure 1:
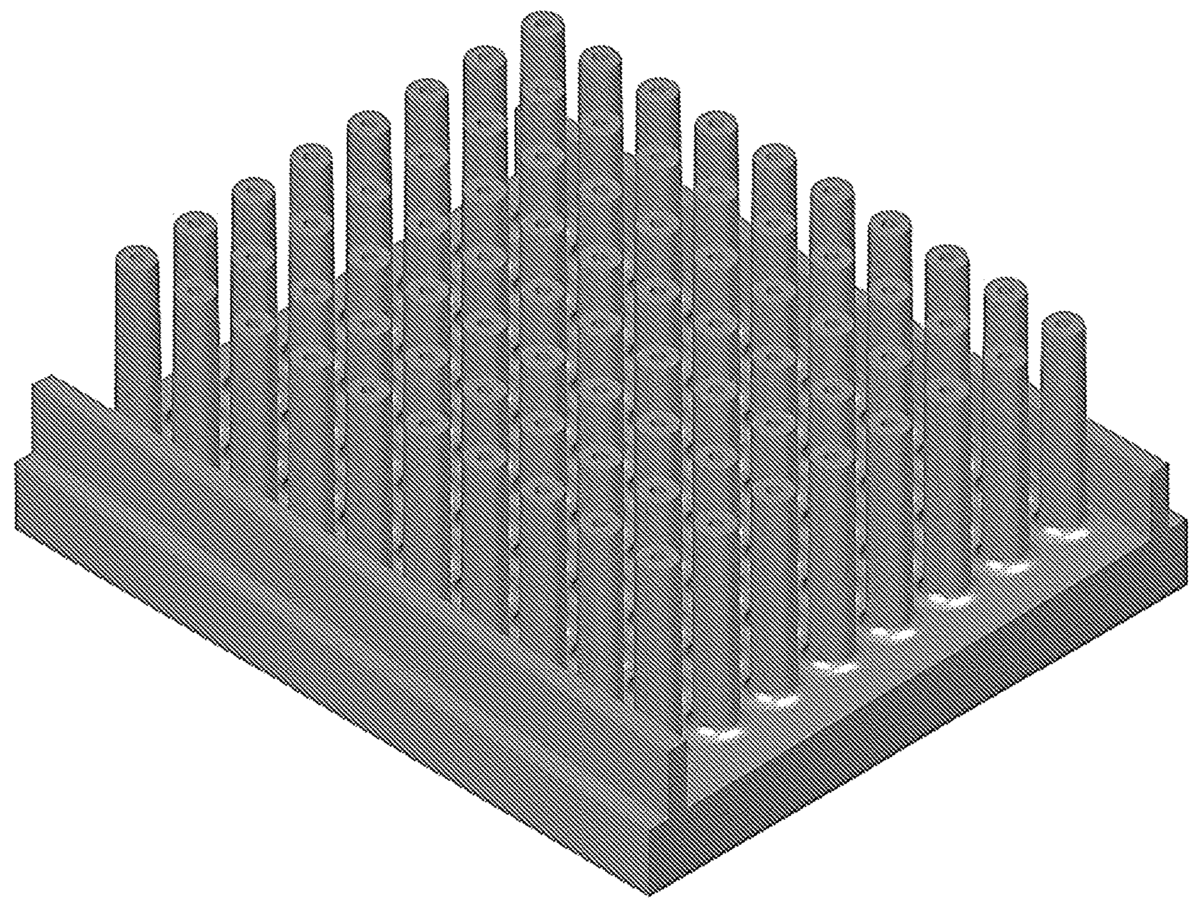
FIG. 1 is a view of an insert for preparing a cell culture chamber in accordance with an embodiment of the invention.

A method for analyzing cells grown in a 3D configuration (spheroids, organoids, or other assemblage) has been created that involves culturing cells in 3D within a histology cassette, such that the cells form the 3D structure(s) there and can then be processed histologically for microscopic analysis without transfer to another receptacle. This method has many advantages including reducing transfer errors, allowing for more efficient sectioning (i.e., fewer cuts are needed to extract cellular material), and compatibility with high throughput devices. In addition, many different cells cultures can now take place within a single histology cassette. This means fewer materials (e.g., histology cassettes, fixative, paraffin, slides, stains, etc.) are being used to create the same amount of cells for downstream processing. This creates efficiencies in handling (e.g., microscopic analysis) and storage, as well. These advantages save investigators significant time and resources.

An embodiment of the invention provides an insert (100) for preparing a cell culture chamber comprising: (a) a base (110) having a base top surface (114), a base bottom surface (115), and at least three base sides (111), and (b) at least one pillar (120) having a pillar top (124), a pillar bottom (125), a pillar first outer diameter (122*a*), a pillar second outer diameter (123*a*), and a pillar outside wall (127), wherein the at least one pillar bottom (125) is contiguous with the base top surface (114), the dimensions of the insert allow for (a) insertion of the at least one pillar (120) of the insert into a hydrogel that is within a histology cassette or (b) placing of a hydrogel around the at least one pillar (120) of the insert when it is in the histology cassette, the pillar second outer diameter (123*a*) creates a cell culture chamber within the hydrogel after the insert is removed from the hydrogel, and the cell culture chamber is suitable for three-dimensional multicellular spheroid growth within the cell culture chamber.

An embodiment of the invention provides an insert (100) for preparing a cell culture chamber in a pliable material, or an array of such cell culture chamber(s), inside a cassette or other receptacle suitable for direct histological processing without the need to transfer the chamber(s) to another receptacle, comprising: (a) a base (110) having a base top surface (114), a base bottom surface (115), and at least three base sides (111), and (b) at least one pillar (120) having a pillar top (124), a pillar bottom (125), a pillar first outer diameter (122*a*), a pillar second outer diameter (123*a*), and a pillar outside wall (127), wherein the at least one pillar bottom (125) is contiguous with the base top surface (114), the dimensions of the insert allow for (a) insertion of the at least one pillar (120) of the insert into a hydrogel that is within a histology cassette or (b) placing of a hydrogel around the at least one pillar (120) of the insert when it is in the histology cassette, the pillar second outer diameter (123*a*) creates a cell culture chamber within the hydrogel after the insert is removed from the hydrogel, and the cell culture chamber is suitable for three-dimensional multicellular spheroid growth within the cell culture chamber. The insert for preparing a cell culture chamber comprises at least three base sides (111). An embodiment of the invention provides a base with four base sides (111). In an embodiment, two of the four base sides (111) may be parallel to each other. In an embodiment, two of the four base sides (111) have the same dimensions thereby forming a rectangular base having a base width, a base length, and a base height. In an embodiment, the insert comprises five, six, seven, eight, nine, or ten base sides (111).

An embodiment of the invention provides an insert comprising at least one solid pillar for preparing a cell culture chamber comprising: (a) a base (110) having a base top surface (114), a base bottom surface (115), and at least three base sides (111), and (b) at least one solid pillar having a pillar top, a pillar bottom, a pillar outer diameter (122*a*), and a pillar outside wall (127), wherein the at least one pillar bottom is contiguous with the base top surface (114), the dimensions of the insert allow for (a) insertion of the at least one solid pillar of the insert into a hydrogel that is within a histology cassette or (b) placing of a hydrogel around the at least one solid pillar of the insert when it is in the histology cassette, the pillar outer diameter (123*a*) creates a cell culture chamber within the hydrogel after the insert is removed from the hydrogel, and the cell culture chamber is suitable for three-dimensional multicellular spheroid growth within the cell culture chamber.

An embodiment of the invention provides an insert comprising at least one solid pillar for preparing a cell culture chamber in a pliable material, or an array of such cell culture chamber(s), inside a cassette or other receptacle suitable for direct histological processing without the need to transfer the chamber(s) to another receptacle, comprising: (a) a base (110) having a base top surface (114), a base bottom surface (115), and at least three base sides (111), and (b) at least one solid pillar having a pillar top, a pillar bottom, a pillar outer diameter (122*a*), and a pillar outside wall (127), wherein the at least one pillar bottom is contiguous with the base top surface (114), the dimensions of the insert allow for (a) insertion of the at least one solid pillar of the insert into a hydrogel that is within a histology cassette or (b) placing of a hydrogel around the at least one solid pillar of the insert when it is in the histology cassette, the pillar outer diameter (123*a*) creates a cell culture chamber within the hydrogel after the insert is removed from the hydrogel, and the cell culture chamber is suitable for three-dimensional multicellular spheroid growth within the cell culture chamber. The insert for preparing a cell culture chamber comprising at least one solid pillar comprises at least three base sides (111). An embodiment of the invention provides a base with four base sides (111). In an embodiment, two of the four base sides (111) may be parallel to each other. In an embodiment, two of the four base sides (111) have the same dimensions thereby forming a rectangular base having a base width, a base length, and a base height. In an embodiment, the insert comprises five, six, seven, eight, nine, or ten base sides (111).

In an embodiment, the base length is from about 15 mm to about 80 mm, from about 15 mm to about 75 mm, from about 15 mm to about 70 mm, from about 15 mm to about 65 mm, from about 15 mm to about 60 mm, from about 15 mm to about 55 mm, from about 15 mm to about 50 mm, from about 15 mm to about 45 mm, from about 15 mm to about 40 mm, from about 15 mm to about 35 mm, from about 15 mm to about 30 mm, from about 15 mm to about 25 mm, from about 15 mm to about 20 mm, or from about 18 mm to about 22 mm. In an embodiment, the base length is the same as, or slightly smaller than, the inner length dimension of a histology cassette. For example, the base length may be about 20 mm or about 30 mm in length. In an alternative embodiment, the base length is longer than the histology cassette such that the insert base may sit on top of the histology cassette while the cell culture chambers are being made out of the hydrogel.

In an embodiment, the base width is from about 15 mm to about 60 mm, from about 15 mm to about 55 mm from about 15 mm to about 50 mm, from about 15 mm to about 45 mm, from about 15 mm to about 40 mm, from about 15 mm to about 35 mm, from about 15 mm to about 30 mm, from about 15 mm to about 25 mm, from about 15 mm to about 20 mm, from about 23 mm to about 27 mm. In an embodiment, the base width is the same as, or slightly smaller than, the inner width dimension of a histology cassette. For example, the base width may be from about 25 mm to about 45 mm in width. In an alternative embodiment, the base width is wider than the histology cassette such that the insert base may sit on top of the histology cassette while the cell culture chambers are being made out of the hydrogel.

In an embodiment, the base height is from about 0.5 mm to about 16 mm, 0.5 mm to about 14 mm, 0.5 mm to about 12 mm, from about 0.5 mm to about 10 mm, from about 0.5 mm to about 8 mm, from about 0.5 mm to about 6 mm, from about 0.5 mm to about 4 mm, from about 1 mm to about 4 mm, from about 2 mm to about 4 mm, or about 3 mm.

Figure 2:
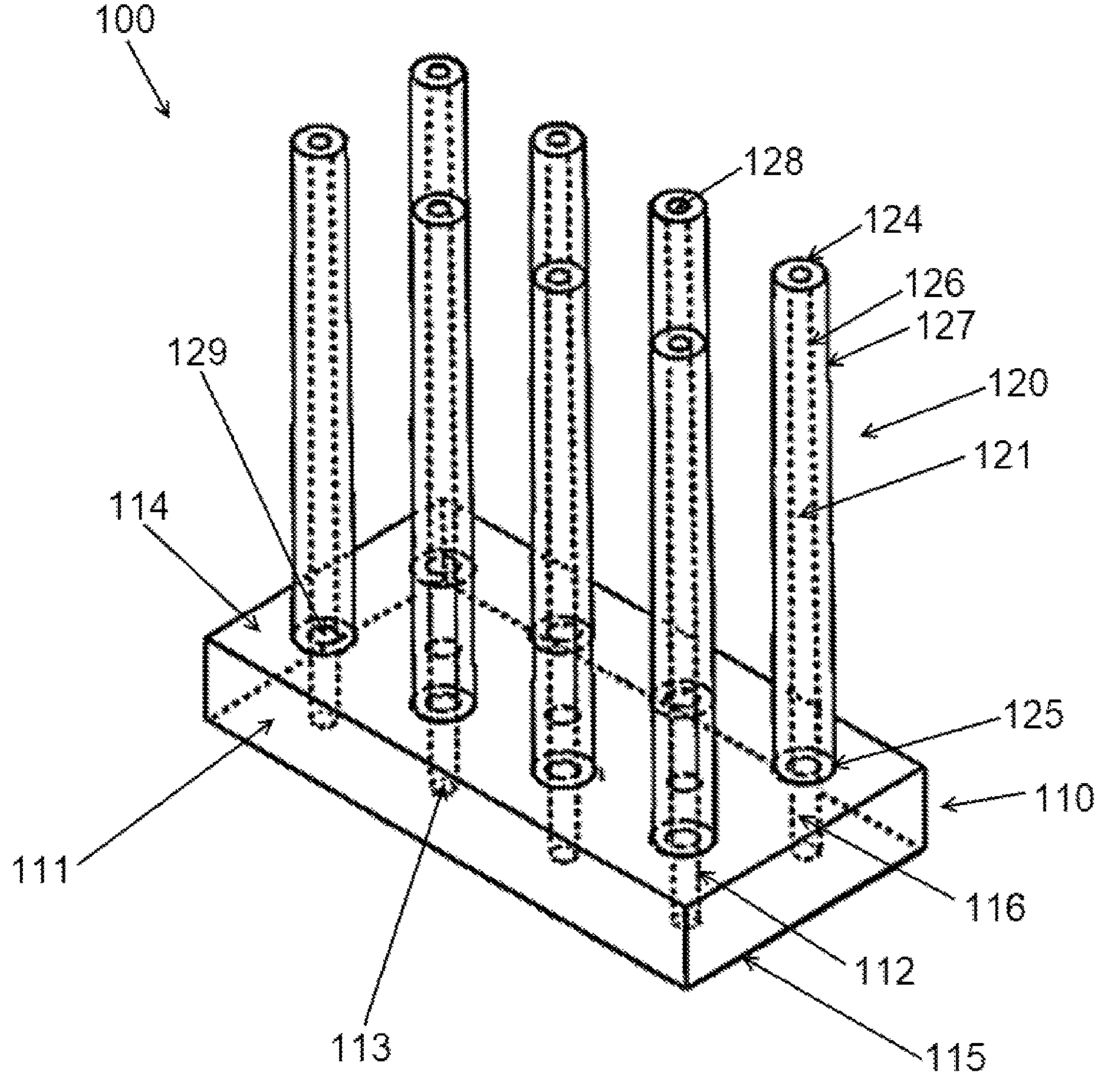
FIG. 2 is a view of an insert for preparing a cell culture chamber in accordance with an embodiment of the invention.
Figure 3:
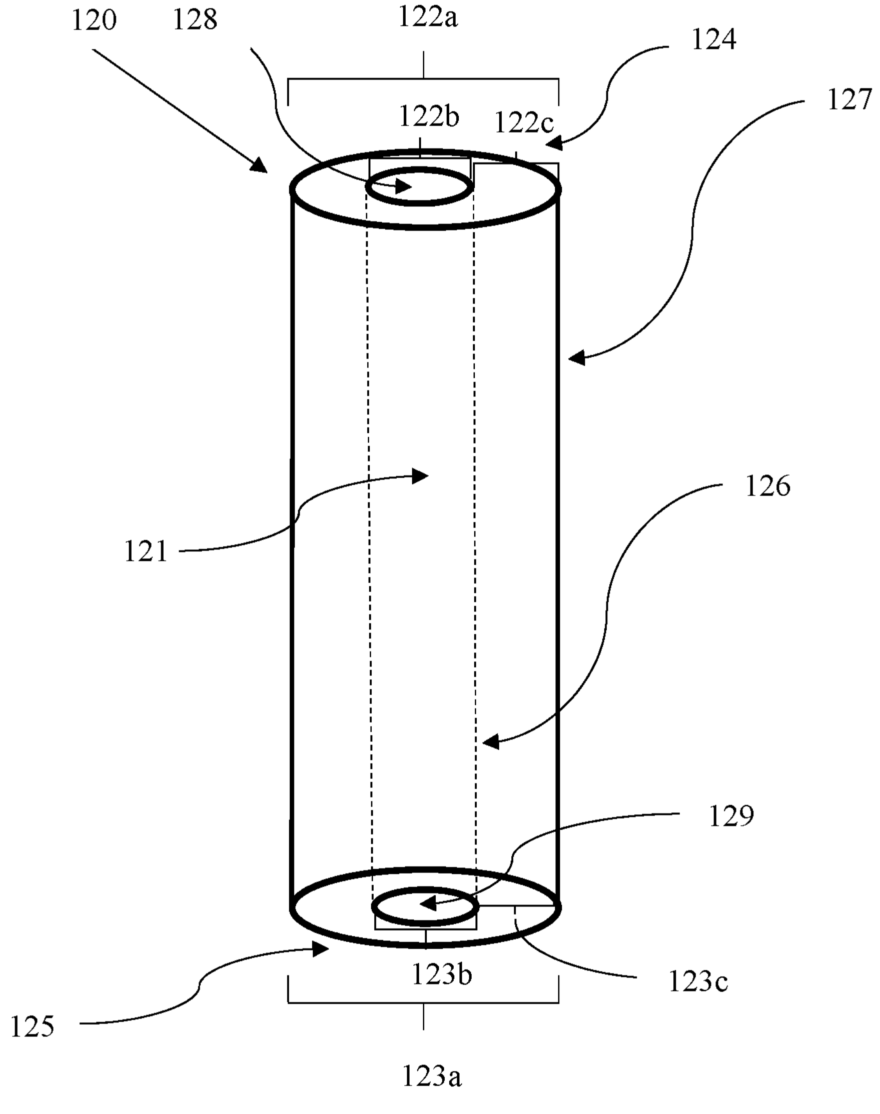
FIG. 3 is a view of a pillar of an insert for preparing a cell culture chamber in accordance with an embodiment of the invention.
Figure 4:
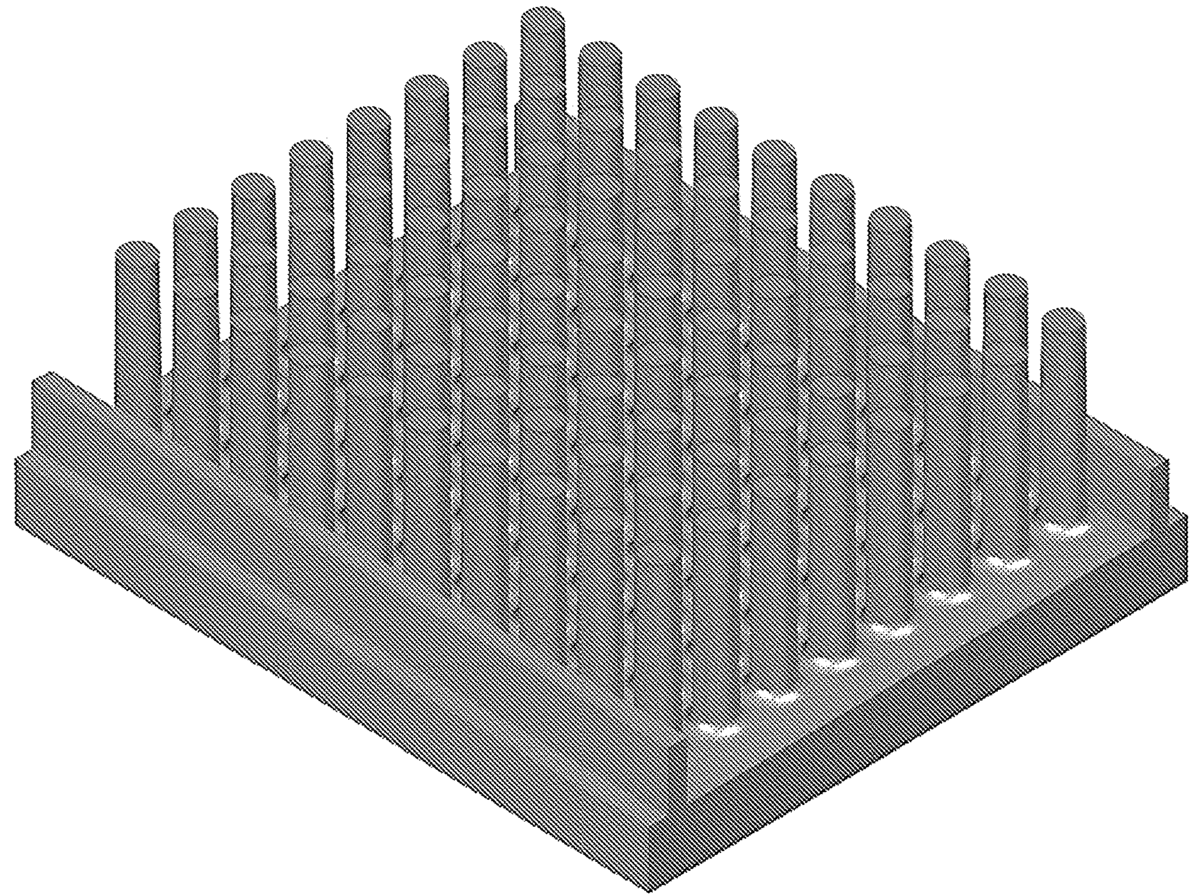
FIG. 4 is a view of an insert for preparing a cell culture chamber in accordance with an embodiment of the invention, wherein the pillars are solid.

In an embodiment, the base has at least one base cavity (116) that extends from the base top surface (114) to the base bottom surface (115), wherein the at least one base cavity is parallel to the at least three base sides (111), and the at least one base cavity creates at least one base inside wall (112) and at least one base inside diameter (113). The base may have the same number of base cavities (116) as it has pillars (120). As seen in FIG. 2, the base cavities may be positioned in the base such that they are aligned with the first pillar inner diameter (122*b*) of a pillar. This exemplary alignment allows for a user to place materials (e.g., load the cells) into the bottom of a cell culture chamber from above the insert while the insert is within the histology cassette.

In an embodiment, the insert comprises at least one pillar (120) having a pillar top (124), a pillar bottom (125), a pillar first outer diameter (122*a*), a pillar second outer diameter (123*a*), and a pillar outside wall (127), wherein the at least one pillar bottom (125) is contiguous with the base top surface (114). The pillars create a space within the hydrogel filled histology cassette for the cells to be cultured. The insert may have any number of pillars as long as they are positioned far enough away from each other that the hydrogel sufficiently separates the cells being cultured. Likewise, the pillars may have any first outer diameter (122*a*) as long as the pillars provide a large enough space within the hydrogel for cells to be cultured and provide enough hydrogel to sufficiently separate the cells being cultured.

In an embodiment, the insert comprises from about 1 to about 6,144 pillars (or any multiple of 6, e.g., 6, 12, 24, 48, 96, 192, 384, 768, and 1,536). In another embodiment, the insert comprises from about 1 to about 100 pillars. In an embodiment, the insert comprises from about 1 to about 8 pillars. In an embodiment, there are 96 pillars, there are 96 pillars arranged on the base in 8 rows of 12, there are 48 pillars, there are 48 pillars arranged on the base in 6 rows of 8, there are 80 pillars, there are 80 pillars arranged on the base in 8 rows of 10, there are about 2 rows of pillars, there are about 2 rows of pillars comprising from about 1 to about 100 pillars, there are about 3 rows of pillars, there are about 3 rows of pillars comprising from about 1 to about 66 pillars, there are about 4 rows of pillars, there are about 4 rows of pillars comprising from about 1 to about 50 pillars, there are about 5 rows of pillars, there are about 5 rows of pillars of comprising from about 1 to about 40 pillars, there are about 6 rows of pillars, there are about 6 rows of pillars comprising from about 1 to about 35 pillars, there are about 7 rows of pillar, there are about 7 rows of pillars comprising from about 1 to about 30 pillars, there are about 8 rows of pillars, there are about 8 pillars comprising from about 1 to about 25 pillars, there are about 9 rows of pillars, there are about 9 rows of pillars comprising from about 1 to about 23 pillars, or there are about 10 rows of pillars, there are about 10 rows of pillars comprising from about 1 to about 20 pillars. In certain embodiments, the insert comprises 96, 192, 384, 768, 1,536, or 6,144 pillars to be compatible with high-throughput screening technology.

In an embodiment, the at least one pillar (120) has a height of from about 0.5 mm to about 12 mm. The at least one pillar, upon removal from the histology cassette filled with hydrogel, creates a cell culture chamber within the histology cassette by displacing hydrogel. Accordingly, the at least one pillar height should be less than the height of the histology cassette such that the at least one pillar does not touch the histology cassette bottom and thereby creates a space between the histology cassette and the pillar top for hydrogel to fill in and create a cell culture chamber bottom.

In an embodiment, the pillar sides are straight such that the pillar first outer diameter (122*a*) has substantially the same diameter as the pillar second outer diameter (123*a*). In an alternative embodiment, the pillars are tapered wherein the pillar first outer diameter (122*a*) is a value that is less than the pillar second outer diameter (123*a*). In an embodiment, the pillar first outer diameter (122*a*) is from about 0.01 mm to about 4.0 mm, from about 0.01 mm to about 3.75 mm, from about 0.01 mm to about 3.5 mm, from about 0.01 mm to about 3.25 mm, from about 0.01 mm to about 3.0 mm, from about 0.01 mm to about 2.75 mm, from about 0.01 mm to about 2.5 mm, from about 0.01 mm to about 2.25 mm, from about 0.01 mm to about 2.0 mm, from about 0.02 to about 2.0 mm, from about 0.04 to about 2.0 mm, from about 0.06 to about 2.0 mm, from about 0.08 to about 2.0 mm, from about 1.0 to about 2.0 mm, from about 1.2 to about 2.0 mm, from about 1.4 to about 1.8 mm, from about 1.5 to about 1.7 mm, or about 1.6 mm. In an embodiment, the pillar second outer diameter (123*a*) is from about 0.01 mm to about 2.0 mm, from about 0.02 to about 2.0 mm, from about 0.04 to about 2.0 mm, from about 0.06 to about 2.0 mm, from about 0.08 to about 2.0 mm, from about 1.0 to about 2.0 mm, from about 1.2 to about 2.0 mm, from about 1.4 to about 1.8 mm, from about 1.5 to about 1.7 mm, or about 1.6 mm.

In an embodiment, the pillar is solid having a pillar top, a pillar bottom, a pillar outer diameter (122*a*), and a pillar outside wall (127), wherein the at least one pillar bottom is contiguous with the base top surface (114).

In an embodiment, the pillar (120) has a pillar cavity creating a pillar inside wall (126), a pillar first wall thickness (122*c*), a pillar first inner diameter (122*b*), a pillar second wall thickness (123*c*), and a pillar second inner diameter (123*b*). In an embodiment, the pillar inside walls (126) are straight such that the pillar first inner diameter (122*b*) and the pillar second inner diameter (123*b*) are substantially the same. In an alternative embodiment, the pillar inside walls (126), are tapered such that the first inner diameter (122*b*) is less than the pillar second inner diameter (123*b*). In an embodiment, the pillar first inner diameter (122*b*) is from about 0.01 mm to about 2 mm, from about 0.01 mm to about 1.75 mm, from about 0.01 mm to about 1.5 mm, from about 0.01 mm to about 1.25 mm, from about 0.05 mm to about 2 mm, from about 0.05 mm to about 1.75 mm, from about 0.05 mm to about 1.5 mm, from about 0.05 mm to about 1.25 mm, from about 0.01 mm to about 1 mm, from about 0.05 mm to about 1 mm, from about 0.1 mm to about 0.9 mm, from about 0.3 mm to about 0.8 mm, from about 0.5 mm to about 0.7 mm, or about 0.6 mm. In an embodiment, the pillar second inner diameter (123*b*) is from about 0.01 mm to about 1 mm, from about 0.05 mm to about 1 mm, from about 0.1 mm to about 0.9 mm, from about 0.3 mm to about 0.8 mm, from about 0.5 mm to about 0.7 mm, or about 0.6 mm.

The pillar first inner diameter is less than the pillar first outer diameter and the pillar second inner diameter is less than the pillar second outer diameter.

In an embodiment, the pillar top (124) is substantially flat. In an alternative embodiment, the pillar top (124) is substantially rounded or otherwise not flat (e.g., may be configured to have an attachment point such as a handle useful for automatic processing equipment).

In an embodiment, the insert may be formed of a substantially rigid, water-insoluble, fluid-impervious, typically thermoplastic material substantially chemically non-reactive with the fluids to be employed in the assays to be carried out with the cell culture chamber(s). The term "substantially rigid" as used herein is intended to mean that the material will resist deformation or warping under a light mechanical and/or thermal load, which deformation would prevent maintenance of the substantially planar surface, although the material may be somewhat elastic. Suitable materials include, for example, plastics, polystyrene or polyvinyl chloride with or without copolymers, derivative polystyrene (so surface is wettable), polyethylenes, polystyrenes, polystyrene-acrylonitrile, polypropylene, polyvinylidine chloride, silicone elastomers (e.g., polydimethylsiloxane) and similar materials. Polystyrene and derivatized polystyrene are materials that may be used as it is the common polymer used for cell culture vessels, inasmuch as it is characterized by very low, non-specific protein binding, making it suitable for use with biometric samples, such as, for example, tissues, cells, blood, viruses and bacteria. Glass is also a suitable material, being used routinely in cell culture vessels and may be washed and sterilized after each use. The base and at least one pillar may be made with the same or different materials. The base and at least one pillar may be attached with or without adhesive. The base and at least one pillar may be made from the same material at the same time such that they are substantially inseparable. The base, at least one pillar, or the insert may be made using 3D printing technology, molding, or by any other suitable means.

In an embodiment, insert must be sterile or sterilizable to work with living cells in culture. Sterilization can occur via autoclaving with high heat, ethylene oxide treatment, alcohol treatment, and other suitable means.

In an embodiment, a hydrogel is used to form the cell culture chambers within the histology cassette. In an embodiment, the hydrogel is collagen. The type of collagen can be selected from any individual or combination of the 28 types of collagen described, including but not limited to fibrillar collagen (e.g. Type I, II, III, V, or XI) and non-fibrillar collagen. Non-fibrillar collagen includes but is not limited to FACIT (Fibril Associated Collagens with Interrupted Triple Helices) (Type IX, XII, XIV, XIX, XXI), short chain (Type VIII, X), basement membrane (Type IV), multiplexin (Multiple Triple Helix domains with Interruptions) (Type XV, XVIII), MACIT (Membrane Associated Collagens with Interrupted Triple Helices) (Type XIII, XVII), microfibril forming (Type VI), and anchoring fibrils (Type VII).

In an embodiment, the hydrogel is a peptide-albumin hydrogel. The hydrogel may be a peptide-albumin hydrogel having a self-assembling, 3-dimensional nanofiber matrix, the nanofiber matrix comprising an amphiphilic peptide and albumin, wherein the peptide comprises a terminal hydrophobic region, a central linker, and a terminal hydrophilic region. Further, the peptide of the hydrogel may comprise amino acid sequence FLIVIGSIIGPGGDGPGGD (SEQ ID NO: 1), or a fragment or variant thereof having at least about 90% homology or about 95% homology to SEQ ID NO: 1, and retains the functional characteristics thereof (for example, PGmatrix, PepGel LLC, Manhattan, KS). See also U.S. Patent Application Publication No. 2016/0030629, which is incorporated herein by reference.

In an embodiment, the cell culture chambers can be formed from layered materials within the histology cassette. Materials can be layered within the cassette in any order and in any thickness needed to provide desired properties. In one aspect, histogel can be layered at the base of the cassette, followed by a layer of gel (e.g. PGmatrix), followed by a layer of media, and completed with a top layer of histogel.

The hydrogel may have a 3-dimensional nanofibrous matrix that is shear thinning (i.e., the viscosity decreases with an increase in the rate of shear stress applied to the gel), but recovers quickly after gel destruction (i.e., is reversible). For example, after the hydrogel is destroyed by subjecting the hydrogel to a sufficient mechanical force (e.g., shear thinning such as placing the pillars of the insert into the hydrogel), the hydrogels have a % recovery of at least about 60%, at least about 80%, at least about 90%, or about 100% in less than about 10 minutes, in less than about 5 minutes, or in less than about 2 minutes (after removing the shear stress from the destroyed gel). As used herein, the "% recovery" of the hydrogel is the percentage of the original storage modulus (i.e., before gel destruction) achieved by the hydrogel after destruction and re-hydrogelation. In other words, shear thinning only temporarily destroys the gel structure/architecture.

The hydrogel should be water soluble and temperature stable up to about 90° C. As used herein, "water soluble" means the hydrogels maybe diluted with water after formation, and "temperature stable" means that the hydrogel is not denatured at temperatures ranging from about 1° C. to about 90° C.

The hydrogels may be prepared by combining the peptides with a source of albumin. As used herein, a "source of albumin" refers to one or more types of (purified) albumin that may be directly combined with the peptides, a composition containing one or more types of albumin, as well as albumin derivatives. The peptide solution comprises the peptides suspended, dispersed, or dissolved in a solvent system at levels of at least about 0.1%, from about 0.1% to about 5% by weight, from about 0.3% to about 3.5% by weight, or from about 0.5% to about 2% by weight, based upon the total weight of the solution taken as 100% by weight. Dried (e.g., freeze-dried) peptides are suitable for used in the hydrogel and may be mixed with the solvent system to create the peptide solution. The peptide solution may have a pH of from about 6 to about 8, from about 6.5 to about 7.5, from about 7 to about 7.5, or about 7. Suitable solvent systems include aqueous alkaline solutions, such as sodium bicarbonate, sodium hydroxide, potassium hydroxide, and mixtures thereof in water.

The peptide solution may be combined with a source of albumin, such as a composition comprising albumin. Suitable types of albumin for use in the hydrogel include albumin isolated, extracted, and/or purified from plant or animal sources, as well as synthesized albumin, such as recombinant/transgenic albumin (e.g., human albumin expressed in a plant system), and derivatives thereof (e.g., modified albumins, such as biotin-labeled, acetylated, glycated, nitrated, etc.). The albumin itself may be directly added to the peptide solutions, or it may be provided as part of a composition that contains albumin. Examples of such compositions include serum, serum-supplemented cell media (e.g., Minimum Essential Medium (MEM), Dulbecco's modified Eagle's medium (DMEM), Roswell Park Memorial Institute medium (RPMI), and Leibovitz medium), and CMRL 1066 (Sigma-Aldrich, St. Louis, MO).

In certain aspects, the level of albumin used in the hydrogel is at least about 0.1% by weight, from about 0.5% by weight to about 20% by weight, or from about 1% by weight to about 10% by weight, based upon the total weight of the peptide-albumin solution taken as 100% by weight. The level of peptide used will vary depending upon the desired function of the hydrogel. In one or more embodiments, the peptide concentration is from about 0.1% by weight to about 10% by weight, from about 0.15% by weight to about 5% by weight, or from about 0.2% by weight to about 1% by weight, based upon the total weight of the peptide-albumin solution taken as 100% by weight. The hydrogel may comprise from about 0.1% to about 3% by weight of the peptide, from about 0.25% to about 1.5% by weight of the peptide, or from about 0.5% to about 1% by weight of the peptide, based on the total weight of the gel taken as 100% by weight. In either the solution or hydrogel, the weight ratio of peptide to albumin may be from about 100:1 to about 1:100, from about 10:1 to about 1:10, or from about 2:1 to about 1:2.

The hydrogels may have a uniform internetwork morphology with a porous structure and open cells. The average cell size of the hydrogel matrix may be from about 10 μm to about 80 μm, from about 20 μm to about 60 μm, or from about 30 μm to about 50 μm, as observed under a scanning electron microscope. The average pore size may range from about 50 to about 200 nm. The hydrogel peptides may be in the form of peptide nanofibers that may have an average diameter of from about 3 nm to about 30 nm, from about 5 nm to about 20 nm, or from about 8 nm to about 15 nm, as measured under a transmission electron microscope. The peptide nanofibers may have an average length of from about 0.3 μm to about 5 μm, from about 0.8 μm to about 3 μm, or from about 1 μm to about 2 μm. The hydrogels may have a storage modulus (associated with gel strength) of at least about 50 Pa, at least about 100 Pa, or from about 100 Pa to about 10,000 Pa (based upon a neutral pH (about 7) and a temperature of about room temperature (aka "ambient temperature" or about 20-25° C.)).

Linear, self-assembling peptides may be used to form the hydrogels. The peptides may comprise three segments or regions: a terminal hydrophobic region, a central linker, and a terminal hydrophilic region. The linker may be positioned between, and optionally directly connected to, the hydrophobic and hydrophilic regions. Thus, the peptides are amphiphilic, with one end segment of the peptide being relatively water loving (i.e., "hydrophilic"), the other end segment of the peptide being relatively water fearing (i.e., "hydrophobic"), and the central linker (turning region) providing the flexibility for turning and folding. A region is considered "hydrophilic" herein, if the region has a greater water affinity than the hydrophobic region of the corresponding peptide. Likewise, a region is considered "hydrophobic" herein, if the region has a greater aversion to water than the respective hydrophilic segment of the corresponding peptide. Accordingly, it will be appreciated that a hydrophobic region may still include one or more hydrophilic amino acid residues, as long as the overall nature of the region is nonetheless more hydrophobic than the corresponding hydrophilic region of the peptide. Similarly, a hydrophilic region may include one or more hydrophobic amino acid residues, as long as the overall nature of the region is nonetheless more hydrophilic than the corresponding hydrophobic region of the peptide. As used herein, it will be appreciated that when referring to amino acids that are present as part of a peptide, the amino acids are actually amino acid residues, regardless of whether "residues" is specifically stated.

The hydrophobic region of the hydrogel may be elastic and capable of binding the Group I and Group II metals (and particularly calcium). Hydrophobic regions may comprise from about 2 to about 15 amino acid residues, from about 4 to about 9 amino acid residues, or about 5 amino acid residues. The amino acid residues may be selected from the group consisting of F, L, I, V, and A. In one or more embodiment, the hydrophobic region is selected from the group consisting of FLIVI (SEQ ID NO: 2), GLIVI (SEQ ID NO: 5), PLIVI (SEQ ID NO: 6), DLIVI (SEQ ID NO: 7), VLIVI (SEQ ID NO: 8), ILIVI (SEQ ID NO: 9), LLIVI (SEQ ID NO: 10), ALIVI (SEQ ID NO: 11), FGIVI (SEQ ID NO: 12), FPIVI (SEQ ID NO: 13), FDIVI (SEQ ID NO: 14), FVIVI (SEQ ID NO: 15), FIIVI (SEQ ID NO: 16), FAIVI (SEQ ID NO: 17), FLGVI (SEQ ID NO: 18), FLPVI (SEQ ID NO: 19), FLDVI (SEQ ID NO: 20), FLVIV (SEQ ID NO: 21), FLAVI (SEQ ID NO: 22), FLIGI (SEQ ID NO: 23), FLIPI (SEQ ID NO: 24), FLIDI (SEQ ID NO: 25), FLIII (SEQ ID NO: 26), FLILI (SEQ ID NO: 27), FLIAI (SEQ ID NO: 28), FLIVG (SEQ ID NO: 29), FLIVP (SEQ ID NO: 30), FLIVD (SEQ ID NO: 31), FLIVV (SEQ ID NO: 32), FLIVL (SEQ ID NO: 33), and FLIVA (SEQ ID NO: 34). In one or more embodiment, the hydrophobic region is FLIVI (SEQ ID NO: 2).

Hydrophilic regions may comprise from about 5 to about 20 amino acid residues, from about 5 to about 10 amino acid residues, or about 10 amino acid residues. The hydrophilic regions may comprise amino acid residues selected from the group consisting of G, P, D, V, I, L, and A. In one or more embodiments, the hydrophilic region is selected from the group consisting of $[GPXXD]_n$ (SEQ ID NO: 35), $[GXXPD]_n$ (SEQ ID NO: 36), $[GXPXID]_n$ (SEQ ID NO: 37), and combinations thereof, where n=1-6, and each X is independently selected from the group consisting of G, A, D, R, Q, E, S, T, K and P. In one embodiment, the hydrophilic region comprises the amino acid residues of $GPGX_1DGPGX_1D$ (SEQ ID NO: 38), where each X1 is independently selected from the group consisting of G and A. In another embodiment, the hydrophilic region may comprise the amino acid residues of $GPGX_1DGPGX_1D$ (SEQ ID NO: 38), wherein each $X_1$ is independently selected from the group consisting of G and A. In a further embodiment, the hydrophilic region comprises or consists of, in order or in any order, amino acid residues of $GPGX_2DGX_3X_2X_2D$ (SEQ ID NO: 39), where each $X_2$ is independently selected from the group consisting of A, G, V, I, and L, and $X_3$ is selected from the group consisting of P, A, G, V, I, and L. In yet another embodiment, the hydrophilic region comprises amino acid residues of $GPGX_2D$ (SEQ ID NO: 40), where $X_2$ is defined above. Furthermore, the hydrophilic region could be selected from the group consisting of amino acid residues of $[GPGX_2DGX_3X_2X_2D]_n$ (SEQ ID NO: 39) and $[GPGX_2D]_n$ (SEQ ID NO: 40), where n is an integer from 1 to 10 or an integer from 1 to 5, and $X_2$ and $X_3$ are defined as above.

The hydrophilic region of the hydrogel may comprise GPGGDGPGGD (SEQ ID NO: 4), or a fragment or variant having at least about 60% homology to SEQ ID NO: 4, and retaining the functional characteristics thereof. The % homology to SEQ ID NO: 4 is at least about 80%, at least about 85%, at least about 90%, at least about 95%, or at least about 98%, and retains the functional characteristics thereof.

The hydrophobic region of the hydrogel may be indirectly connected to the hydrophilic region and include a linker. The linker provides structural flexibility which allows the potentially charged side-chains of the hydrophilic residues to come in proximity and help the segregation of hydrophobic and non-hydrophobic side-chains. Suitable hydrogel linkers comprise from about 1 to about 12 amino acid residues, from about 4 to about 8 amino acid residues, or 4 amino acid residues. The hydrogel linkers may comprise amino acids residues selected from the group consisting of G, L, I, V, A, S, and T. The hydrogel linker may be selected from the group consisting of G, GG, GGG, GGGG (SEQ ID NO: 41), $GSX_4X_4$ (SEQ ID NO: 42), $X_4GSX_4$ (SEQ ID NO: 43), $X_4X_4GS$ (SEQ ID NO: 44), $SGX_4X_4$ (SEQ ID NO: 45), $X_4SGX_4$ (SEQ ID NO: 46), $X_4X_4SG$ (SEQ ID NO: 47), $GX_4SX_4$ (SEQ ID NO: 48), $X_4GX_4S$ (SEQ ID NO: 49), $SX_4GX_4$ (SEQ ID NO: 50), $X_4SX_4G$ (SEQ ID NO: 51), $GX_4X_4S$ (SEQ ID NO: 52), and $SX_4X_4G$ (SEQ ID NO: 53), where each $X_4$ is independently selected from the group consisting of G, I, V, A, L, S (and where S could be replaced by T in all sequences listed). The hydrogel linker may comprise or consist of, amino acid residues of $X_5SX_6X_6$ (SEQ ID NO: 54), where $X_5$ is selected from the group consisting of G, I, and V, and each $X_6$ is independently selected from the group consisting of G, I, V. A, and L. At least one of X5 or X6 may be G. In one embodiment, S of $X_5SX_6X_6$ (SEQ ID NO: 54) could be replaced with T. In one or more embodiment, the linker is GSII (SEQ ID NO: 3).

The peptides of the hydrogel may be short peptides. The peptides may have less than about 30 amino acid residues, less than about 20 amino acid residues, or 19 amino acid residues. The peptide may comprise (consist essentially or even consist of) the amino acid sequence FLIV-IGSIIGPGGDGPGGD (SEQ ID NO: 1), or a fragment or variant thereof having at least about 60% homology, at least about 80% homology, at least about 85% homology, at least about 90% homology, at least about 95% homology, or at least about 98% homology to SEQ ID NO: 1, and retaining the functional characteristics thereof.

The cell culture chamber is created within a histology cassette. Standard histology cassettes (e.g., regulars or deeps or so-called "Mega cassettes") may be used with the inserts and the histology cassettes may be sterile or non-sterile. For example, the histology cassette may have the dimensions (length×width×height) of about 30 mm× about 40 mm× about 11 mm, about 53 mm× about 75 mm× about 12 mm, about 40 mm× about 25 mm× about 10 mm, about 40 mm× about 26 mm× about 13 mm, or about 41 mm× about 28 mm× about 13 mm. The histology cassettes may be reusable metal cassettes or disposable (e.g., made of plastic). The inserts may also be modified such that the pillars fit the inner dimensions of the histology cassettes. The base of the insert may be larger than the inner dimensions of the histology cassette such that the base may sit on top of the histology cassette when the cell culture chambers are being made out of the hydrogel by the pillars extending into the histology cassette. The inner dimensions of the histology cassette may be from about 20 mm to about 30 mm in length, from about 25 mm to about 45 mm in width, and from about 2 mm to about 7 mm in height. The inner dimensions of the histology cassette may be from about 25 mm to about 58 mm in length, from about 20 mm to about 85 mm in width, and from about 8 mm to about 15 mm in height. The inner dimensions of the histology cassette may be from about 30 mm to about 53 mm in length, from about 25 mm to about 75 mm in width, and from about 10 mm to about 13 mm in height. Alternatively, the inner dimensions of the histology cassette may be from about 75 mm to about 85 mm in length, from about 40 mm to about 60 mm in width, and from about 2 mm to about 7 mm in height.

The cell culture chambers may be made at least two different ways using the inserts. For example, the at least one pillar of the insert may be placed into a hydrogel that is within a histology cassette and then the insert may be removed from the hydrogel and the histology cassette to create the at least one cell culture chamber within the histology cassette. Alternatively, the at least one pillar of the insert may be placed within a histology cassette and then a hydrogel may be placed into the histology cassette. When the insert is removed from the hydrogel and the histology cassette, the at least one cell culture chamber within the histology cassette is created. The hydrogel may be placed in the histology cassette using any suitable means, for example, by injecting or pouring. The cells may be introduced either after removing the insert or with the insert in place by using internal channels.

A further embodiment of the invention provides systems for growing three-dimensional multicellular spheroids comprising culturing cells within the at least one cell culture chamber prepared using the insert of the present invention to produce three-dimensional multicellular spheroids. The at least one cell culture chamber may be created using the insert in any of the methods disclosed herein.

The three-dimensional multicellular spheroids may be from cells of any desired origin. For example, cancer cell lines, stem cells, primary cells, normal cells, and neuron cells may be used. In that regard, the cells can be from the following origins may be used: bladder, bone, brain, breast, colon, ovary, uterus, head, neck, blood, liver, lymph, pancreas, soft tissue, and stomach. Cells from a patient sample may also be used, for example, from a tumor biopsy. Human and non-human cells may be used.

Fluid (e.g., cell media, buffer, or a solution) may be used in the systems of the present invention. For example, a cell media may be added into and/or around the cell culture chambers to facilitate growth of the cell into the three-dimensional multicellular spheroids. The fluid may prevent the cells and hydrogel from drying out.

A further embodiment of the invention provides systems for analyzing at least one cultured cell in vitro comprising: (a) culturing a cell (or cells) within the at least one cell culture chamber prepared using the insert of the present invention to produce three-dimensional multicellular spheroids; (b) fixing the three-dimensional multicellular spheroids within the at least one cell culture chamber; (c) embedding the three-dimensional multicellular spheroids within the at least one cell culture chamber; (d) sectioning the three-dimensional multicellular spheroids; (e) staining the three-dimensional multicellular spheroids; and (f) assessing the properties of the three-dimensional multicellular spheroids based on the level of staining, wherein the three-dimensional multicellular spheroids are cultured, fixed, and embedded while within a histology cassette.

The three-dimensional multicellular spheroids may be fixed using any suitable means including chemical or physical methods. Physical methods of fixation include heating, micro-waving, and cryo-preservation (freeze drying). Chemical methods of fixation include immersion of the three-dimensional multicellular spheroids in the fixative (e.g., formalin solution).

The three-dimensional multicellular spheroids may be embedded using any suitable means including using wax (e.g., paraffin).

The three-dimensional multicellular spheroids may be sectioned using any suitable means, including using a microtome to cut the embedded three-dimensional multicellular spheroids.

The three-dimensional multicellular spheroids may be mounted onto slides, if desired. The three-dimensional multicellular spheroids may be mounted to the slides using any suitable means. The slides may be cover slipped, if desired.

The three-dimensional multicellular spheroids may be stained using any suitable means. For example, the three-dimensional multicellular spheroids may be stained with Hematoxylin and Eosin (H&E) to analyze the cell morphology. The H&E staining process may involve the steps of dewaxing, dehydration, hematoxylin exposure, differentiation, bluing, eosin exposure, dehydration, clearing, and cover slipping.

Alternatively or in addition, the three-dimensional multicellular spheroids may be processed such that they may be analyzed via immunohistochemistry, in situ hybridization (e.g., fluorescence in situ hybridization (FISH) and RNASCOPE™, Advanced Cell Diagnostics, Newark, CA), immunofluorescence microscopy (e.g., using labeled antibodies), laser capture microdissection, or using the NCOUNTER™ System (NanoString Technologies, Inc., Seattle, Washington).

The three-dimensional multicellular spheroids may be compatible with high-throughput screening of the three-dimensional multicellular spheroids. For example, the three-dimensional multicellular spheroids may be subjected to screening for biomarkers or gene expression. In this regard, the inserts may have 96, 192, 384, 768, 1,536, or 6,144 pillars thereby creating 96, 192, 384, 768, 1,536, or 6,144 cell culture chambers, respectively.

The design of the inserts, and the methods and systems that use the inserts, may benefit the investigator by allowing the cells to grow into three-dimensional multicellular spheroids at approximately the same axial registration in each cell culture chamber such that following embedding, the multicellular structures are present within a single section cut and may be analyzed on the same slide.

Examples of Non-Limiting Aspects of the Disclosure

Aspects, including embodiments, of the present subject matter described herein may be beneficial alone or in combination, with one or more other aspects or embodiments. Without limiting the foregoing description, certain non-limiting aspects of the disclosure numbered 1-30 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. An insert for preparing a cell culture chamber comprising:
(a) a base having a base top surface, a base bottom surface, and at least three base sides, and
(b) at least one pillar having a pillar top, a pillar bottom, a pillar first outer diameter at the pillar top, a pillar second outer diameter at the pillar bottom, and a pillar outside wall, wherein the at least one pillar bottom is contiguous with the base top surface, the dimensions of the insert allow for (a) insertion of the at least one pillar of the insert into a hydrogel that is within a histology cassette or (b) placing of a hydrogel around the at least one pillar of the insert when it is in the histology cassette, the pillar second outer diameter creates a cell culture chamber within the hydrogel after the insert is removed from the hydrogel, and the cell culture chamber is suitable for three-dimensional multicellular spheroid growth within the cell culture chamber.
2. The insert of aspect 1, wherein the hydrogel is a peptide-albumin hydrogel or a collagen hydrogel.
3. The insert of aspect 1 or 2, wherein the hydrogel is a peptide-albumin hydrogel and the peptide-albumin hydrogel has a self-assembling, 3-dimensional nanofiber matrix, the nanofiber matrix comprising an amphiphilic peptide and albumin, wherein the peptide comprises a terminal hydrophobic region, a central linker, and a terminal hydrophilic region.
4. The insert of aspect 3, wherein the peptide comprises the amino acid sequence FLIVIGSIIGPGGDGPGGD (SEQ ID NO: 1), or a fragment or variant thereof having at least about 90% homology to SEQ ID NO: 1, and retaining the functional characteristics thereof.
5. The insert of aspect 1 or 2, wherein the hydrogel is a collagen hydrogel.
6. The insert of aspect 1, 2 or 5, wherein the hydrogel comprises one or more of Type I collagen, Type II collagen, Type III collagen, Type IV collagen and Type V collagen.
7. The insert of aspect 1 or 2, wherein the hydrogel is a layered material.
8. The insert of aspect 1, 2 or 7, wherein the hydrogel comprises a layered material which comprises a first layer of histogel, a layer of PGmatrix, a layer of media, and a second layer of histogel.
9. The insert of any one of aspects 1-8, wherein the base has four base sides.
10. The insert of aspect 9, wherein two of the four base sides that are parallel to each other have the same dimensions thereby forming a rectangular base having a base width, a base length, and a base height.
11. The insert of aspect 10, wherein the base length is from about 15 mm to about 80 mm.
12. The insert of aspect 10 or 11, wherein the base width is from about 15 mm to about 60 mm.
13. The insert of any one of aspects 10-12, wherein the base height is from about 0.5 mm to about 16 mm.
14. The insert of any one of aspects 10-13, wherein the base length is from about 15 to about 80 mm, the base width is from about 15 mm to about 60 mm, and the base height is from about 0.5 mm to about 16 mm.
15. The insert of any one of aspects 1-14, wherein the base has at least one base cavity that extends from the base top surface to the base bottom surface, wherein the at least one base cavity is parallel to the at least three base sides, and the at least one base cavity creates at least one base inside wall and at least one base inside diameter.
16. The insert of any one of aspects 1-15, wherein from about 1 to about 6,144 pillars are contiguous with the base.
17. The insert of any one of aspects 1-16, wherein there are 80 pillars contiguous with the base.
18. The insert of aspect 17, wherein the 80 pillars are arranged on the base in 8 rows of 10.
19. The insert of any one of aspects 1-18, wherein a height of the at least one pillar is from about 0.5 mm to about 15 mm.

20. The insert of any one of aspects 1-19, wherein the at least one pillar first outer diameter s from about 0.01 mm to about 4 mm.

21. The insert of any one of aspects 1-20, wherein the pillar second outer diameter is from about 0.01 mm to about 4 mm.

22. The insert of aspect 20 or 21, wherein the pillar first outer diameter is less than the pillar second outer diameter.

23. The insert of any one of aspects 1-22, wherein the at least one pillar is a solid pillar.

24. The insert of any one of aspects 1-22, wherein the at least one pillar has a pillar cavity creating a pillar inside wall, a pillar first wall thickness at the top of the pillar, a pillar first inner diameter at the top of the pillar, a pillar second wall thickness at the bottom of the pillar, and a pillar second inner diameter at the bottom of the pillar.

25. The insert of aspect 24, wherein the pillar first inner diameter is from about 0.01 mm to about 2 mm.

26. The insert of aspect 24 or 25, wherein the pillar second inner diameter is from about 0.01 mm to about 2 mm.

27. The insert of any one of aspects 24-26, wherein the pillar first inner diameter is less than the pillar second inner diameter.

28. The insert of any one of aspects 1-27, wherein the inner dimensions of the histology cassette are from about 20 mm to about 30 mm in length, from about 25 mm to about 45 mm in width, and from about 2 mm to about 7 mm in height.

29. The insert of any one of aspects 1-27, wherein the inner dimensions of the histology cassette are from about 75 mm to about 85 mm in length, from about 40 mm to about 60 mm in width, and from about 2 mm to about 7 mm in height.

30. A method of preparing at least one cell culture chamber comprising:
(a) placing the at least one pillar of the insert of any one of aspects 1-29 into a hydrogel that is within a histology cassette; and
(b) removing the insert from the hydrogel and the histology cassette to create the at least one cell culture chamber within the histology cassette.

31. A method of preparing at least one cell culture chamber comprising:
(a) placing the at least one pillar of the insert of any one of aspects 1-29 within a histology cassette,
(b) placing a hydrogel into the histology cassette; and
(c) removing the insert from the hydrogel and the histology cassette to create the at least one cell culture chamber within the histology cassette.

32. A system for growing three-dimensional multicellular spheroids comprising: culturing cells within the at least one cell culture chamber prepared using the insert of any one of aspects 1-29 to produce three-dimensional multicellular spheroids.

33. The system of aspect 32, wherein the method of aspect 30 or 31 is used to prepare the at least one cell culture chamber.

34. A system for analyzing at least one cultured cell in vitro comprising:
(a) culturing a cell within the at least one cell culture chamber prepared using the insert of any one of aspects 1-29 to produce three-dimensional multicellular spheroids;
(b) fixing the three-dimensional multicellular spheroids within the at least one cell culture chamber;
(c) embedding the three-dimensional multicellular spheroids within the at least one cell culture chamber;
(d) sectioning the three-dimensional multicellular spheroids;
(e) staining the three-dimensional multicellular spheroids; and
(f) assessing the properties of the three-dimensional multicellular spheroids based on the level of staining, wherein the three-dimensional multicellular spheroids are cultured, fixed, and embedded while within a histology cassette.

35. The system of aspect 34, wherein the system is compatible with high-throughput screening of the three-dimensional multicellular spheroids.

Example 1

This example demonstrates that the present inserts successfully create suitable cell culture chambers.

An insert was created using a 3D printer with 8 rows of 10 pillars. The pillars had dimensions that were suitable for cell culturing. The pillars of the insert were placed in sterile standard sized histology cassettes and a soft biocompatible polymer (e.g., a peptide hydrogel) was poured around the insert. The insert was then removed from the cassette creating the cell culture chambers. Three-dimensional multicellular spheroids were successfully cultured within the cell culture chambers.

Example 2

This example demonstrates that the present inserts successfully create suitable cell culture chambers.

An insert was created using a 3D printer with 8 rows of 10 pillars. The pillars had dimensions that were suitable for cell culturing. A soft biocompatible polymer (e.g., a peptide hydrogel) was poured into a sterile standard sized histology cassette. The pillars of the insert were then pressed into the soft biocompatible polymer thereby displacing the soft biocompatible polymer and creating cell culture chambers. Three-dimensional multicellular spheroids were successfully cultured within the cell culture chambers.

Example 3

This example demonstrates that the present inserts are suitable for analysis of three-dimensional multicellular spheroids.

The three-dimensional multicellular spheroids of Examples 1 and 2 were subsequently processed and analyzed. Following successful cell culturing, the three-dimensional multicellular spheroids were fixed using a suitable fixing agent (e.g., formalin) within the cell culture chambers, then embedded using a suitable embedding medium (e.g., paraffin), then sectioned, mounted on microscope slides, stained, and cover slipped. The three-dimensional multicellular spheroids were then microscopically visualized and assessed for properties based on their level of staining.

Example 4

This example demonstrates that the present inserts are suitable for high throughput analysis of three-dimensional multicellular spheroids.

Inserts were created with 48 and 96 cuboidal pillars and used to create cell culture chambers. The cell culture chambers were then used to successfully culture three-dimensional multicellular spheroids. The three-dimensional multicellular spheroids were then subjected to high-throughput analysis.

TABLE 1

| List of Reference Numbers | |
|---|---|
| Number | Part |
| 100 | Insert |
| 110 | Base of Insert |
| 111 | Base side |
| 112 | Base inside wall |
| 113 | Base inside diameter |
| 114 | Base top surface |
| 115 | Base bottom surface |
| 116 | Base cavity |
| 120 | Pillar |
| 121 | Pillar cavity |
| 122a | Pillar first outer diameter |
| 122b | Pillar first inner diameter |
| 122c | Pillar first wall thickness |
| 123a | Pillar second outer diameter |
| 123b | Pillar second inner diameter |
| 123c | Pillar second wall thickness |
| 124 | Pillar top |
| 125 | Pillar bottom |
| 126 | Pillar inside wall |
| 127 | Pillar outside wall |
| 128 | Pillar top opening |
| 129 | Pillar base opening |

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and “at least one” and similar referents in the context of describing the invention (especially in the context of the following claims) are to be construed to cover both the singular and the plural, unless otherwise indicated herein or clearly contradicted by context. The use of the term “at least one” followed by a list of one or more items (for example, “at least one of A and B”) is to be construed to mean one item selected from the listed items (A or B) or any combination of two or more of the listed items (A and B), unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for analyzing at least one cultured cell in vitro comprising:

(a) placing at least one pillar of an insert into a hydrogel that is within a histology cassette, wherein the insert comprises:

(i) a base having a base top surface, a base bottom surface, and at least three base sides, and (ii) at least one pillar having a pillar top, a pillar bottom, a pillar first outer diameter at the pillar top, a pillar second outer diameter at the pillar bottom, and a pillar outside wall, wherein the at least one pillar bottom is contiguous with the base top surface, and wherein the at least one pillar has a pillar cavity creating a pillar inside wall, a pillar first wall thickness at the pillar top, a pillar first inner diameter at the pillar top, a pillar second wall thickness at the pillar bottom, and a pillar second inner diameter at the pillar bottom;

(b) removing the insert from the hydrogel and the histology cassette to create at least one cell culture chamber within the histology cassette;

(c) culturing a cell within the at least one cell culture chamber to produce three-dimensional multicellular spheroids;

(d) fixing the three-dimensional multicellular spheroids within the at least one cell culture chamber;

(e) embedding the three-dimensional multicellular spheroids within the at least one cell culture chamber;

(f) sectioning the embedded three-dimensional multicellular spheroids;

(g) staining the three-dimensional multicellular spheroids; and (h) assessing the properties of the three-dimensional multicellular spheroids based on the level of staining, wherein the three-dimensional multicellular spheroids are cultured, fixed, and embedded while within a histology cassette.

2. The method of claim 1, further comprising performing high-throughput screening of the three-dimensional multicellular spheroids.

3. The method of claim 1, wherein the hydrogel is selected from the group consisting of a peptide-albumin hydrogel, a collagen hydrogel, a hydrogel comprised of layered materials and any combination thereof.

4. The method of claim 1, wherein the hydrogel is a peptide-albumin hydrogel and the peptide-albumin hydrogel has a self-assembling, 3-dimensional nanofiber matrix, the nanofiber matrix comprising an amphiphilic peptide and albumin, wherein the peptide comprises a terminal hydrophobic region, a central linker, and a terminal hydrophilic region.

5. The method of claim 4, wherein the peptide comprises the amino acid sequence FLIVIGSIIGPGGDGPGGD (SEQ ID NO: 1), or a fragment or variant thereof having at least about 90% homology to SEQ ID NO: 1, and retaining the functional characteristics thereof.

6. The method of claim 1, wherein the hydrogel is a collagen hydrogel.

7. The method of claim 1, wherein the hydrogel comprises one or more of Type I collagen, Type II collagen, Type III collagen, Type IV collagen, Type V collagen, and Type VI collagen.

8. The method of claim 1, wherein the hydrogel is a layered material.

9. A method for analyzing at least one cultured cell in vitro comprising:

(a) placing at least one pillar of an insert within a histology cassette, wherein the insert comprises:
  (i) a base having a base top surface, a base bottom surface, and at least three base sides, and
  (ii) at least one pillar having a pillar top, a pillar bottom, a pillar first outer diameter at the pillar top, a pillar second outer diameter at the pillar bottom, and a pillar outside wall, wherein the at least one pillar bottom is contiguous with the base top surface, and wherein the at least one pillar has a pillar cavity creating a pillar inside wall, a pillar first wall thickness at the pillar top, a pillar first inner diameter at the pillar top, a pillar second wall thickness at the pillar bottom, and a pillar second inner diameter at the pillar bottom;
(b) placing a hydrogel into the histology cassette;
(c) removing the insert from the hydrogel and the histology cassette to create at least one cell culture chamber within the histology cassette;
(d) culturing a cell within the at least one cell culture chamber to produce three-dimensional multicellular spheroids;
(e) fixing the three-dimensional multicellular spheroids within the at least one cell culture chamber;
(f) embedding the three-dimensional multicellular spheroids within the at least one cell culture chamber;
(g) sectioning the embedded three-dimensional multicellular spheroids;
(h) staining the three-dimensional multicellular spheroids; and
(i) assessing the properties of the three-dimensional multicellular spheroids based on the level of staining, wherein the three-dimensional multicellular spheroids are cultured, fixed, and embedded while within a histology cassette.

10. The method of claim 9, further comprising performing high-throughput screening of the three-dimensional multicellular spheroids.

11. The method of claim 9, wherein the hydrogel is selected from the group consisting of a peptide-albumin hydrogel, a collagen hydrogel, a hydrogel comprised of layered materials and any combination thereof.

12. The method of claim 9, wherein the hydrogel is a peptide-albumin hydrogel and the peptide-albumin hydrogel has a self-assembling, 3-dimensional nanofiber matrix, the nanofiber matrix comprising an amphiphilic peptide and albumin, wherein the peptide comprises a terminal hydrophobic region, a central linker, and a terminal hydrophilic region.

13. The method of claim 12, wherein the peptide comprises the amino acid sequence FLIVIGSIIGPGGDGPGGD (SEQ ID NO: 1), or a fragment or variant thereof having at least about 90% homology to SEQ ID NO: 1, and retaining the functional characteristics thereof.

14. The method of claim 9, wherein the hydrogel is a collagen hydrogel.

15. The method of claim 9, wherein the hydrogel comprises one or more of Type I collagen, Type II collagen, Type III collagen, Type IV collagen, Type V collagen, and Type VI collagen.

16. The method of claim 9, wherein the hydrogel is a layered material.

17. The method of claim 1, comprising, prior to step (b), depositing at least one cell through the pillar cavity, and thereby depositing the at least one cell into the hydrogel.

18. The method of claim 1, wherein a height of the at least one pillar is from about 0.5 mm to about 15 mm;

wherein the pillar first outer diameter is from about 0.01 mm to about 4 mm, and the pillar second outer diameter is from about 0.01 mm to about 4 mm; and wherein the pillar first inner diameter is from about 0.01 mm to about 2 mm, and the pillar second inner diameter is from about 0.01 mm to about 2 mm.

19. The method of claim 9, comprising, prior to step (c), depositing at least one cell through the pillar cavity, and thereby depositing the at least one cell into the hydrogel.

20. The method of claim 9, wherein a height of the at least one pillar is from about 0.5 mm to about 15 mm;

wherein the pillar first outer diameter is from about 0.01 mm to about 4 mm, and the pillar second outer diameter is from about 0.01 mm to about 4 mm; and wherein the pillar first inner diameter is from about 0.01 mm to about 2 mm, and the pillar second inner diameter is from about 0.01 mm to about 2 mm.

* * * * *